United States Patent [19]

Schlenoff et al.

[11] Patent Number: 5,552,551

[45] Date of Patent: Sep. 3, 1996

[54] PROTON-TRANSFER, LOW SELF-ABSORBING CHROMOPHORES FOR USE IN SCINTILLATORS

[75] Inventors: Joseph B. Schlenoff; Kurtis F. Johnson; Jayesh Dharia; Feng Gao, all of Tallahassee, Fla.

[73] Assignee: Florida State University, Tallahassee, Fla.

[21] Appl. No.: 96,956

[22] Filed: Jul. 26, 1995

Related U.S. Application Data

[63] Continuation-in-part of Ser. No. 874,748, Apr. 27, 1992, Pat. No. 5,258,478.

[51] Int. Cl.$^6$ .................... C07D 215/20; C07D 311/76; C07D 311/22
[52] U.S. Cl. ........................................... 546/155; 549/400
[58] Field of Search .................... 549/400, 402; 546/156, 155

[56] References Cited

U.S. PATENT DOCUMENTS

| | | | |
|---|---|---|---|
| 3,985,566 | 10/1976 | Buhr et al. | 96/115 R |
| 4,011,266 | 3/1977 | Pearson et al. | 260/590 FB |
| 4,452,720 | 6/1984 | Harada et al. | 252/301.16 |
| 4,591,600 | 5/1986 | Creuzet et al. | 514/456 |
| 4,758,679 | 7/1988 | Schmitthenner | 549/403 |
| 5,100,587 | 3/1992 | Clough et al. | 252/646 |
| 5,110,500 | 5/1992 | Walker | 252/301.16 |

OTHER PUBLICATIONS

Qualitz et al., "Pressure-sensitive recording material with improved stability, fading resistance and heat resistance", Chem. Abstr. 96: 208445p (1982) p. 608.

Zorn et al., "Pilot study of new radiation-resistant plastic scintillators doped with 3–hydroxyflavone", Chem. Abstr. 110: 30241m (1989) p. 422.

Flavonoids From Chemotrypes of the Goldback Fern, Pityrogramma Triangularis, Wollenweber et al., 24(5), pp. 965–971, 1985.

"Synthesis of 3,6–Dimethoxy–6", 6"–dimethylchromeno (7,8: 2", 3") flavone", Gupta et al., vol. 19B, pp. 616–617, 1980.

F. M. Dean and Verapong Podimuang, Journal of Chemical Society 1965 (Jul.), 3978–87.

Primary Examiner—Joseph L. Schofer
Assistant Examiner—Wu C. Cheng
Attorney, Agent, or Firm—Senniger, Powers, Leavitt & Roedel

[57] ABSTRACT

Proton-transfer, low self-absorbing chromophores of the formula:

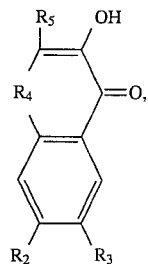

wherein $R_2$ and $R_3$ are independently hydrogen, alkyl, aryl, cyano, nitro, halo or an ether group, $R_4$ is O or N—H, and $R_5$ is thienyl, naphthyl, furanyl, pyrrolyl, phenyl vinyl, diphenyl vinyl, phenyl ethynyl, hydroxy chromonyl phenyl, didecyloxy hydroxy chromonyl phenyl, phenyl or

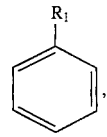

wherein $R_1$ is vinyl, vinyl phenyl, vinyl benzyl, alkyl ethenyl, or alkyl phenyl ethenyl, provided that when $R_5$ is phenyl and $R_2$ and $R_3$ are hydrogen, $R_4$ is N—H.

37 Claims, No Drawings

PROTON-TRANSFER, LOW SELF-ABSORBING CHROMOPHORES FOR USE IN SCINTILLATORS

CROSS REFERENCE TO RELATED APPLICATION

This application is a continuation-in-part of application Serial No. 07/874,748, filed Apr. 27, 1992 now U.S. Pat. No. 5,258,478.

BACKGROUND OF THE INVENTION

This invention relates to dyes useful as fluorescent materials. More specifically, it relates to proton-transfer, low self-absorbing dyes particularly useful in scintillating detectors for high-energy radiation and particles. The dyes comprise novel chromophores exhibiting properties which enhance the performance of such scintillating detectors.

The detection of high-energy radiation can be accomplished through the use of compounds which scintillate (emit light) when a particle of radiation impinges on, or passes near, such compounds. Organic molecules capable of light emission based on fluorescence are called fluors, or chromophores. In the process of fluorescence, a chromophore is excited by absorbing an energy source, such as a photon, and then emits a photon of lower energy (longer wavelength) upon relaxation. Excitation of chromophores can also be produced by radiationless transfer of energy or by other high energy processes. Thus, the ability of chromophores to scintillate in this manner makes them a useful material for the detection or tracking of ionizing particles.

In current technological applications, chromophores are typically dispersed in a plastic medium, such as polystyrene. The term "scintillator" is applied to the polymer/chromophore ensemble.

A particularly useful chromophore is 3-hydroxyflavone (3HF). 3HF has the formula:

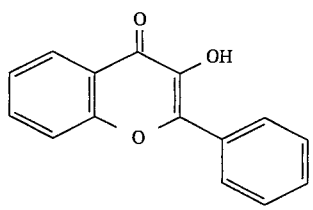

3HF is the chromophore of choice for many commercial scintillators because it emits a significantly longer wavelength than it absorbs. On excitation, a proton is transferred to the carbonyl group of the 3HF molecule in the following manner:

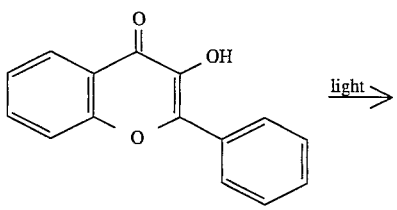

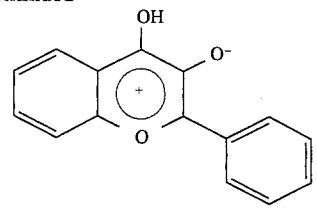

This property, known as proton-transfer fluorescence, produces a greater Stokes shift (the difference in absorbed and emitted wavelengths) for the 3HF molecule than occurs in other chromophore molecules. This enhanced Stokes shift is commercially significant in several respects. First, it bypasses radiation-induced color centers in the plastic medium which attenuate the light output of the scintillator and shorten its useful life. Second, 3HF's greater Stokes shift makes it a low self-absorbing fluor, since photons emitted at greatly reduced wavelengths are much less likely to be reabsorbed by another chromophore before exiting the scintillator.

While scintillators utilizing 3HF molecules dissolved in a plastic matrix are preferable to alternative scintillating materials for the reasons discussed above, they are not without shortcomings. For instance, there is a limit to the solubility of 3HF in plastics. Typically, scintillators using 3HF chromophores are limited to a chromophore concentration of about 1.2% (by weight at room temperature). This restricts the maximum level of brightness to which 3HF scintillators are capable. Further, over time, scintillators using chromophore molecules dispersed in a plastic medium are subject to chromophore migration and phase separation. This phenomenon adversely affects the quality of the scintillation produced by the material and reduces the useful life of the scintillator.

Scintillators comprising 3HF molecules are also limited as to other features important in detectors for high-energy radiation, such as their extinction coefficients, their quantum efficiency and their ability to red-shift emissions.

SUMMARY OF THE INVENTION

Among the objects of the invention, therefore, may be noted the provision of proton-transfer, low self-absorbing chromophores exhibiting one or more of the following characteristics: increased solubility in or capacity to be chemically bound to the plastic medium in which they are dispersed; improved brightness; reduced chromophore migration; higher extinction coefficients; increased quantum efficiency; and enhanced ability to red-shift emissions; and the provision of a process for the preparation of intrinsically scintillating polymers containing such chromophores chemically bound to the polymer.

Briefly, therefore, the present invention is directed to a chromophore of the formula:

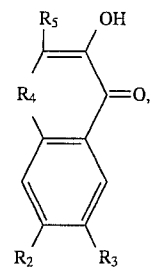

wherein $R_2$ and $R_3$ are independently hydrogen, alkyl, aryl, cyano, nitro, halo or an ether group, $R_4$ is O or N—H, and $R_5$ is thienyl, naphthyl, furanyl, pyrrolyl, phenyl vinyl, diphenyl vinyl, phenyl ethynyl, hydroxy chromonyl phenyl, didecyloxy hydroxy chromonyl phenyl, phenyl or

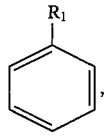

wherein $R_1$ is vinyl, vinyl phenyl, vinyl benzyl, alkyl ethenyl, or alkyl phenyl ethenyl, provided that when $R_5$ is phenyl and $R_2$ and $R_3$ are hydrogen, $R_4$ is N—H.

The present invention is further directed to a polymerizable chromophore of the formula:

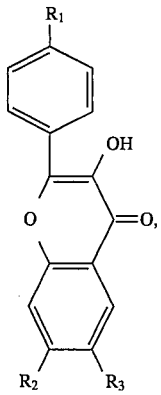

2 wherein $R_1$ is vinyl, vinyl phenyl, vinyl benzyl, alkyl ethenyl or alkyl phenyl ethenyl, $R_2$ and $R_3$ are independently hydrogen, alkyl, aryl, cyano, nitro, halo, or an ether group.

The present invention is also directed to a process for the preparation of an intrinsically scintillating polymer having a repeating unit in the polymer chain derived from a chromophore of the formula:

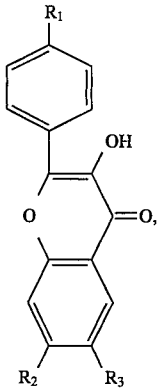

2 wherein $R_1$ is vinyl, vinyl phenyl, vinyl benzyl, alkyl ethenyl or alkyl phenyl ethenyl and $R_2$ and $R_3$ are independently hydrogen, alkyl, aryl, cyano, nitro, halo, or ether, comprising contacting an aldehyde having an unsaturated aliphatic moiety with 2-hydroxyacetophenone to produce a hydroxyflavone monomer and polymerizing the monomer using a radical initiator.

Other objects and features will be in part apparent and in part pointed out hereinafter.

DESCRIPTION OF THE PREFERRED EMBODIMENT

In accordance with the present invention it has been discovered that, by utilizing the synthetic route disclosed by the present invention, proton-transfer, low self-absorbing chromophores with improved properties for use in scintillating detectors have been developed. These novel chromophores exhibit one or more advantageous properties, including higher extinction coefficients, increased quantum efficiency and an enhanced ability to red-shift emissions. Certain of these novel dyes exhibit increased solubility in the plastic medium used as the solvent for such scintillators, particularly those novel chromophores which include a covalently bonded unsaturated alkyl moiety. These chromophores may be utilized in the production of low self-absorbing, intrinsically scintillating polymers having limitless chromophore solubility, brighter fluorescence, and which are not subject to chromophore migration and phase separation. These scintillating polymers will also undergo copolymerization reactions with other plastic materials, such as polystyrene.

The present invention is directed to chromophore 1 and its derivatives, the structure of which is depicted below.

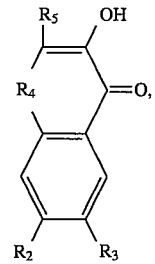

1

As discussed above, $R_2$ and $R_3$ are independently hydrogen, alkyl, aryl, cyano, nitro, halo or an ether group, $R_4$ is O or N—H, and $R_5$ is thienyl, naphthyl, furanyl, pyrrolyl, phenyl vinyl, diphenyl vinyl, phenyl ethynyl, hydroxy chromonyl phenyl, didecyloxy hydroxy chromonyl phenyl, phenyl or

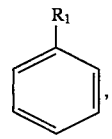

wherein $R_1$ is vinyl, vinyl phenyl, vinyl benzyl, alkyl ethenyl, or alkyl phenyl ethenyl. When $R_5$ is phenyl and $R_2$ and $R_3$ are hydrogen, $R_4$ is N—H.

Certain chromophores within the general formula 1 detailed above, are polymerizable. The structure of such polymerizable chromophores is depicted below.

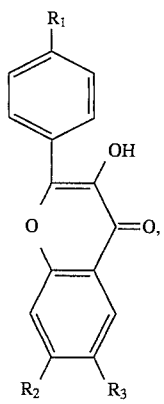

In this embodiment of the invention, $R_1$ is vinyl, vinyl phenyl, vinyl benzyl, alkyl ethenyl or alkyl phenyl ethenyl, and $R_2$ and $R_3$ are independently hydrogen, alkyl, aryl, cyano, nitro, halo, or ether.

The structure of a preferred chromophore, in which $R_1$ is vinyl and $R_2$ and $R_3$ are both hydrogen is shown below:

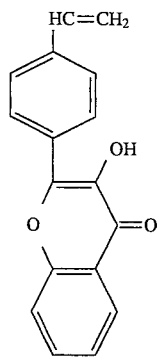

According to IUPAC rules, the name of chromophore 2 is 4'-vinyl, 3-hydroxyflavone.

Proton-transfer, low self-absorbing chromophores of the type depicted in formula 1 above may be produced by contacting an aldehyde with a 2-hydroxyacetophenone under certain prescribed conditions. As a general illustration of such a reaction scheme, the reaction for the synthesis of a polymerizable 3HF from an aldehyde and 2-hydroxyacetophenone is depicted as follows:

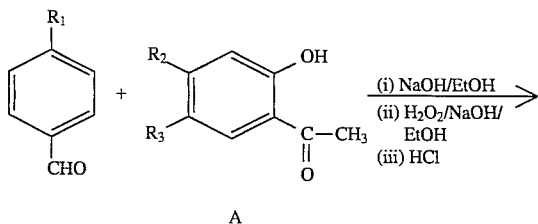

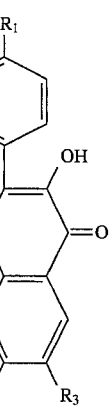

The substituents $R_1$, $R_2$ and $R_3$ are as defined above.

In a particularly preferred procedure, 4-vinyl benzaldehyde is prepared from 4-chlorostyrene and combined with 2-hydroxyacetophenone in an ethyl alcohol solution to which NaOH is added. After allowing the reaction mixture to sit at room temperature overnight, a solution of hydrogen peroxide in aqueous ethyl alcohol is added and the reaction mixture is acidified to complete the preparation of 4'-vinyl 3-hydroxyflavone.

Alternatively, a vinyl phenyl hydroxyflavone may be prepared by synthesizing 4-styrene trimethyltin and combining it with 4-bromobenzaldehyde to produce 4'-vinyl, 4-biphenyl aldehyde. This intermediate compound is then reacted with 2-hydroxyacetophenone to produce the vinyl phenyl hydroxyflavone. This reaction scheme proceeds as follows:

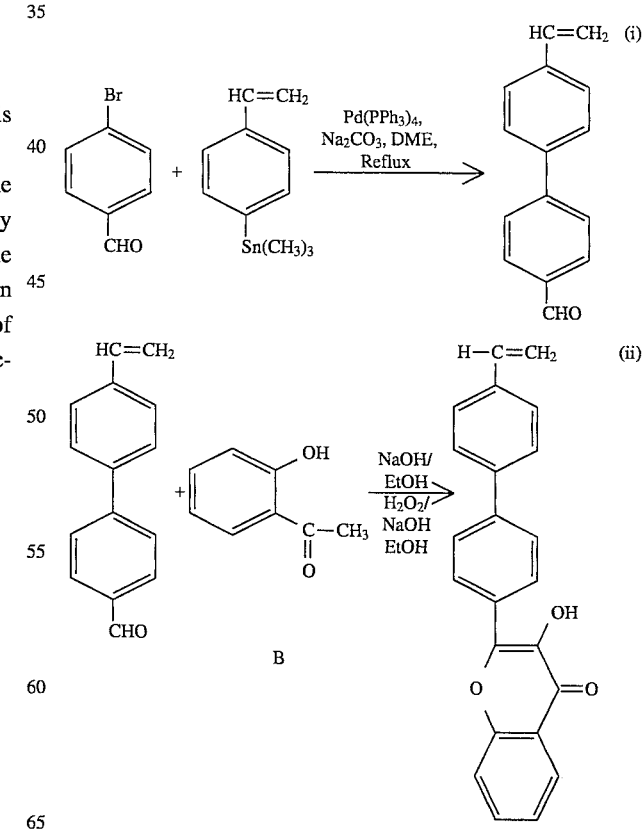

A third approach to the preparation of proton-transfer, low self-absorbing chromophores of the type described herein is exemplified by the preparation of vinyl 3HF using a synthetic route which calls for the preparation of 4'-vinyl, 4-aldehyde diphenylmethane by combining 4-trimethyltin styrene with bromomethylbenzaldehyde. The 4'-vinyl, 4-aldehyde diphenylmethane may then be combined with 2-hydroxyacetophenone as described above for conversion to vinyl benzyl 3HF. This reaction scheme is set forth as follows:

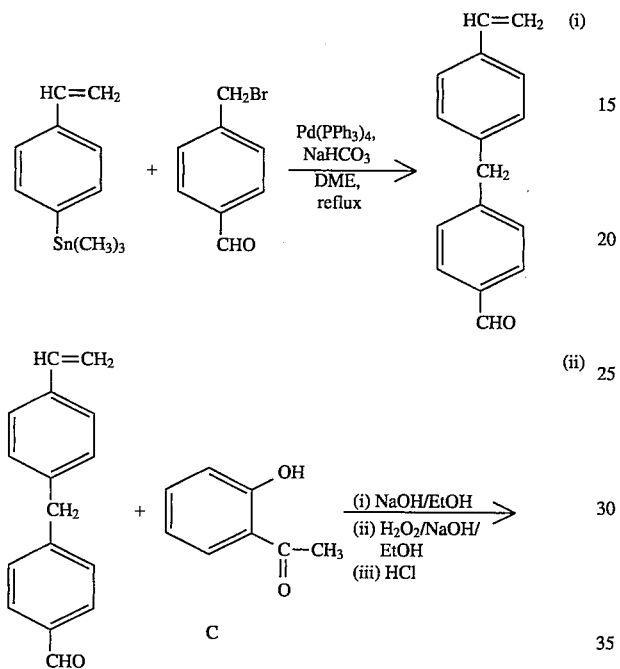

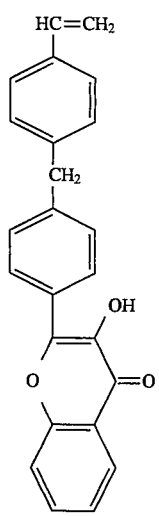

The hydrogens at the $R_2$ and $R_3$ positions of chromophore 1, as well as hydrogens attached to the vinylic carbons at $R_1$ may be replaced by a number of substituents without significantly affecting the ability of the dyes of this invention to be used effectively in scintillating detectors, and in particular, the vinyl 3HFs of this invention to function effectively as polymerizable chromophores. Among the functional groups which may readily replace the hydrogens at these positions are alkyl, aryl, cyano, nitro, halo, or ether. Alkyl groups are preferably $C_{1-10}$ alkyl, and most preferably, methyl or ethyl. Aryl groups are preferably $C_{6-15}$ aryl, and most preferably, phenyl. Exemplary compounds within the generic formula are depicted hereinbelow:

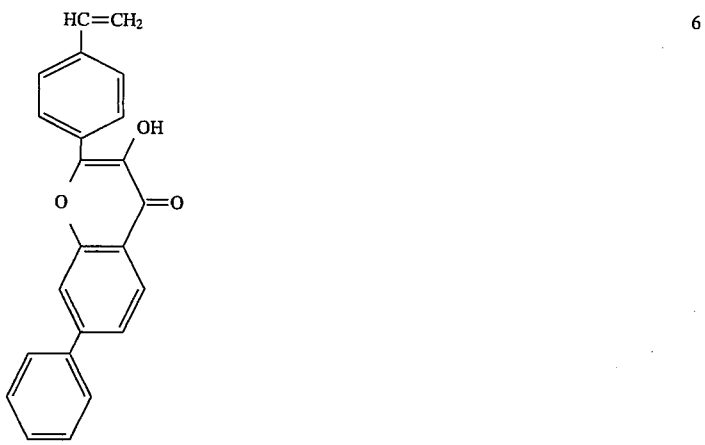

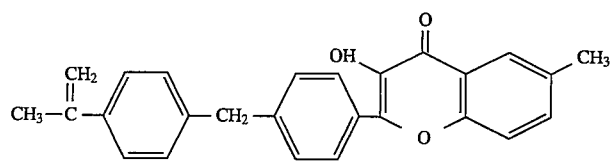

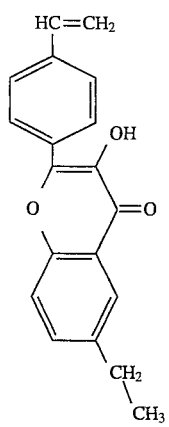
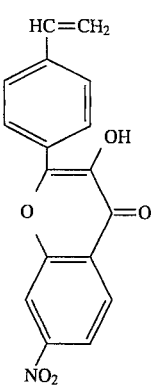
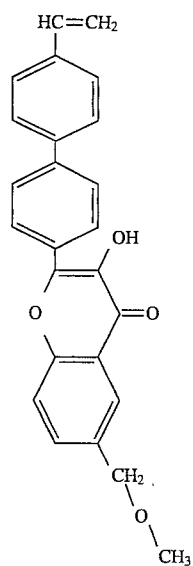
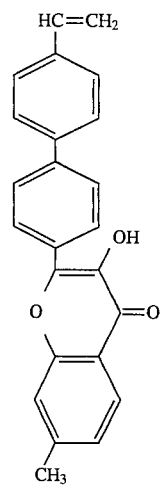
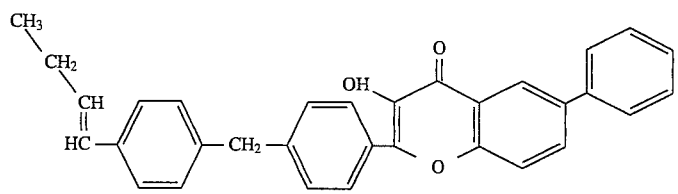

11
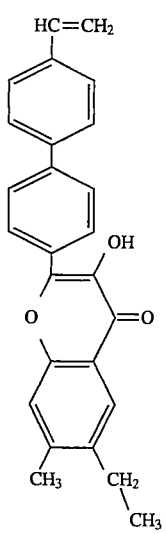
12
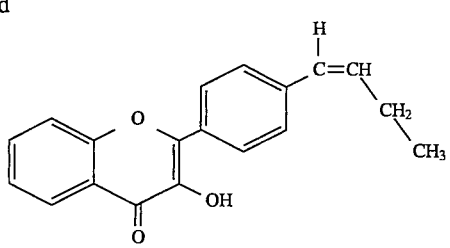
14
16
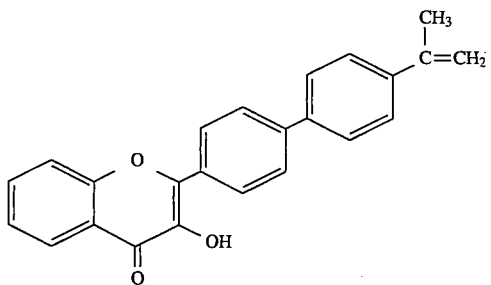
15
17
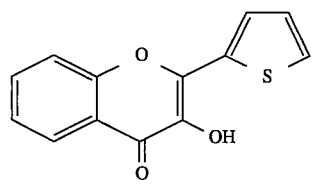
18
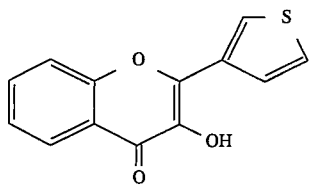
19
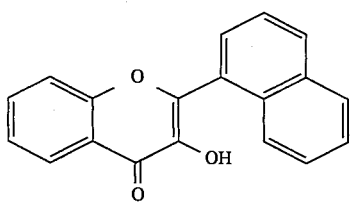
20
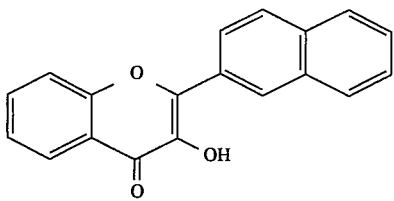
21
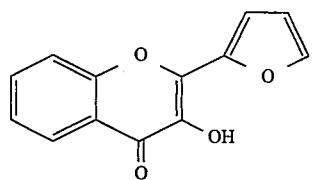
22
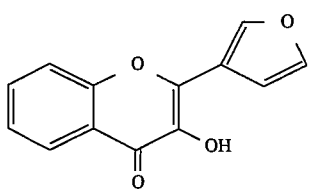
23
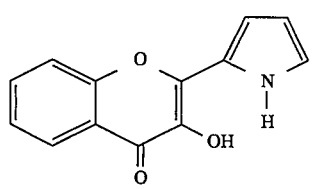
24
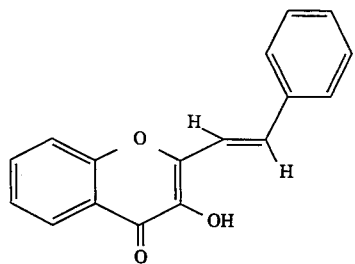
25
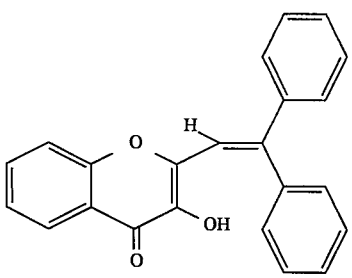

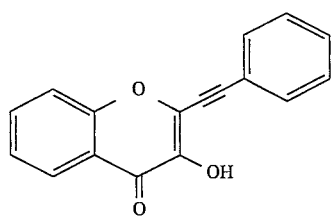

26
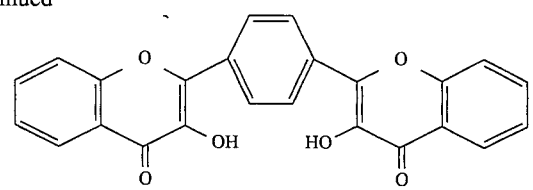

27

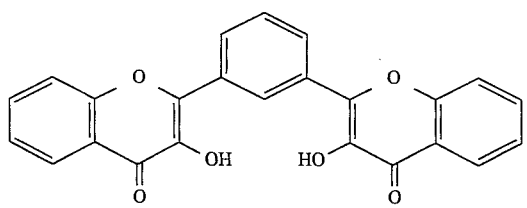

28
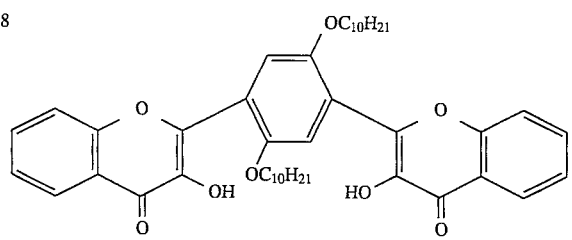

29

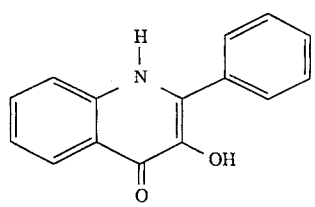

30

In accordance with the process of the present invention, a poly(vinyl)-3HF is prepared which may be utilized as a scintillator. In this process, polymerizable HF monomer (chromophore 2) is prepared by contacting 2-hydroxyacetophenone with an aldehyde having an unsaturated aliphatic moiety, for example, using one of the reaction schemes discussed above. The 3HF monomer thus produced is then polymerized using a radical initiator such as azobisisobutyronitrile (AIBN). A representative example of the above-described polymerization reaction is depicted as follows:

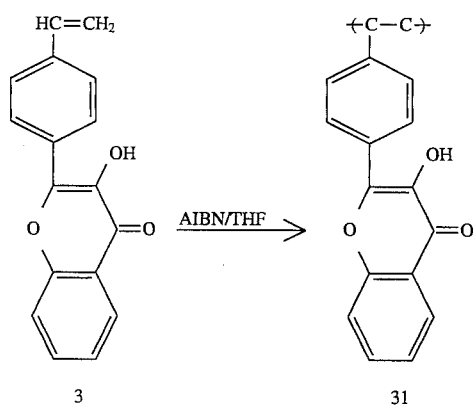

Co-polymers consisting of repeating units derived from unsaturated alkyl 3HF and at least one other polymerizable monomer may also be produced according to the method of this invention. Copolymers using different weight percentages of unsaturated alkyl 3HF may be prepared using a radical initiator as discussed above. The polymerizable 3HF monomer is combined with another monomer, such as styrene, in a desired ratio of the monomers. An example of a copolymer produced by the copolymerization reaction of vinyl 3HF and styrene is set forth below:

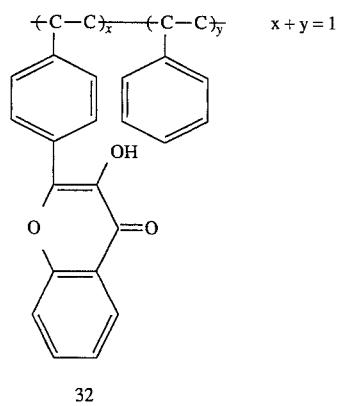

32

The same procedure may be utilized to create a copolymer of vinyl 3HF with other repeating units in the polymer chain. For example, vinyl 3HF monomer may be combined with either vinyl toluene or methyl methacrylate monomer in selected proportions to produce copolymers having a predetermined ratio of vinyl 3HF to the other monomer.

The vinyl 3HF polymers and copolymers of this invention produce films which may be used as scintillators. For example, these scintillating polymers may be used to detect ionizing radiation emanating from particle accelerators. Preferably, for use as scintillators the chromophore concentration of the polymer is between about 0.5% and about 10% (by weight), and most preferably, about 5%.

A polymer comprising 5% by weight vinyl 3HF will scintillate with substantially greater brightness than 3HF dissolved in a plastic medium, which has a maximum solubility of about 1.2%. Additionally, chromophore migration and phase separation between the chromophores and the plastic are prevented since the chromophore units are covalently bonded to the polymer. Further, the high concentration of chromophores ameliorates the loss in light output due to irradiation damage.

The chromophores of this invention also exhibit one or more advantageous properties, including higher extinction coefficients, increased quantum efficiency and an enhanced ability to red-shift emissions. For example, 3-hydroxy-4'-(α-methyl), ethenylphenyl) flavone (Example 10) exhibits an extinction coefficient more than two-and-one-half times that of 3HF ($\epsilon_{max}$ (m$^{-1}$cm$^{-1}$)=14000) and a quantum yield 80% greater than that achieved by 3HF, while trans-3-hydroxy-2-(β-phenylvinyl)-4H-1-benzopyran-4-one (Example 15) demonstrates a significantly enhanced red-shift ($\lambda_{max\ (em)}$=600 nm vs. $\lambda_{max}$ (em)=530 for 3HF).

The following examples illustrate the invention:

EXAMPLE 1

Preparation of 4'-Vinyl 3-Hydroxy Flavone (4'V3HF)

a) 4-vinyl Benzaldehyde 4-chlorostyrene (Fluka) was dried over CaH$_2$ prior to use. Anhydrous dimethyl formamide (DMF) (Aldrich) was used as received. THF was dried over sodium benzophenone complex and was distilled prior to use. All glassware used was flame dried and cooled under dry nitrogen prior to use. Nitrogen was passed through a column of silica blue and drient. A standard cannular transfer technique was used to transfer air sensitive reagents.

7.6 gms (0.312 moles) of Mg tunings were transferred to an RB flask containing 50 ml of dry THF under nitrogen atmosphere. 2 ml of ethyl bromide was then added to the Mg metal and the reaction mixture was warmed to 50°–55° C. The mixture reacted vigorously and activated Mg metal was formed. A solution of 20 ml (0.156 moles) of 4-chlorostyrene in 50 ml of THF was added dropwise at room temperature to the activated Mg. The reaction mixture was stirred for an additional two hours. A dark gray solution appeared and was allowed to settle down. In a separate 1L RB flask, a solution of 12 ml (0.15 moles) of anhydrous DMF was prepared in 300 ml of THF. The DMF solution was cooled in an icebath under dry nitrogen atmosphere for 15 mins. Grignard reagent was added dropwise to the DMF solution over a period of 1 hr with vigorous stirring. The reaction flask was then allowed to stir for three hrs. at 5° C. and RT overnight. The reaction was quenched by pouring the entire reaction mixture into 300 ml of dilute HCl in an icebath. The product was separated by solvent extraction with ether. The ether layer was dried over anhyd. MgSO$_4$ and filtered. Finally, ether was evaporated under reduced pressure. A viscous yellow liquid was obtained and was dried under vacuum for 2 hrs and stored in a freezer at −10° C. containing a small amount of hydroquinone as an inhibitor. A yield of 65% high purity (above 95%) 4-vinyl benzaldehyde was obtained.

b) 4'-vinyl-3-hydroxyflavone 2-hydroxyacetophenone (Aldrich) was used as received. Ethyl alcohol was distilled prior to use. 4-vinyl benzaldehyde was synthesized using the procedure described in Example 1(a).

13 gms of 4-vinyl benzaldehyde (0.955 moles) was added to a flask containing 13.9 gms of 2-hydroxyacetophenone (0.955) in 150 ml alcohol. In a separate RB flask, 13 gms of NaOH was dissolved in 100 ml of aqueous ethyl alcohol (75%). The NaOH solution was added to the reaction mixture at once. The color of the solution immediately changed from colorless to yellow to pink, and then, finally, to a dark red precipitate. The solution was allowed to sit at room temperature overnight. The next morning, 6 gms of NaOH in 200 ml of aqueous ethyl alcohol (75%) was added to the precipitate and the reaction mixture was cooled in an icebath for 15 mins. In a separate RB flask, a solution of 50 ml of 30% hydrogen peroxide solution in 50 ml of aqueous ethyl alcohol (75%) was added to the reaction flask at once at 0°–5° C. The red colored precipitate dissolved immediately and the color of the solution slowly changed from red to yellow. The solution was gradually warmed to room temperature and was stirred for 6 hrs. The reaction mixture was neutralized with dil. HCl at 0°–4° C. A white precipitate formed and was filtered and washed with distilled water until it was free from acid. The color of the product slowly changed from colorless to light pink or to light brown during filtration.

The vinyl 3HF produced was purified by washing with alcohol followed by recrystallization from dry THF. Yield of the product isolated after the first purification was 13.5 gms (50%).

EXAMPLE 2

4'-styryl-3-hydroxyflavone a) 4-trimethyltin Styrene

Grignard reagent was added to a flask containing 18 ml of trimethyltin chloride in 250 ml of THF at −78° C. The reaction mixture was stirred at −78° C. for 3 hrs and RT overnight under nitrogen atmosphere. The reaction mixture was poured into 300 ml of dil. HCl and followed by extraction by 2 portions of 200 ml of solvent ether. The ether layer was dried over anhydrous MgSO$_4$ and filtered. The ether was then evaporated under reduced pressure. A light yellow viscous liquid was obtained, poured into pentane and kept in a freezer overnight. A white precipitate was produced, which was filtered off. Pentane was evaporated under reduced pressure. A light yellow viscous liquid was obtained and was dried under vacuum overnight. A yield of 68% was obtained.

b) 4'-vinyl, 4-biphenyl Aldehyde 1.4 gms (0.075 moles) of 4-bromobenzaldehyde was mixed with 400 mg of Pd(PPh$_3$)$_4$ catalyst in dry box under an argon atmosphere. 50 ml of ethylene glycol dimethyl ether was added under nitrogen atmosphere and refluxed for 1 hr. In a separate flask, a solution of 2.25 gms (0.15 moles) of styrene trimethyltin was prepared in 20 ml of ethylene glycol dimethyl ether and flushed with nitrogen for 25 minutes. This was dropwise added to the reaction flask containing bromobenzaldehyde and Pd(PPh$_3$)$_4$ catalyst. This was followed by the addition of 2 ml of saturated NaHCO$_3$. The reaction mixture was warmed to 60° C. for 48 hrs, after which the reaction was quenched by pouring the reaction mixture into 300 ml of water. 4'-vinyl, 4-biphenyl aldehyde was extracted with three 200 ml extracts of solvent ether. The ether layer was dried over MgSO$_4$ and filtered. Ether was evaporated under reduced pressure. A dark yellow precipitate was obtained and was washed with 200 ml of pentane. A dark yellow residue left after washing with pentane was discarded. The pentane solution was concentrated and 4'-vinyl, 4-biphenyl aldehyde was isolated by recrystallization at low temperature. A white precipitate was obtained, which was filtered and dried under vacuum overnight.

c) 4'styryl, 3-hydroxyflavone 180 mg of 4'-vinyl, 4-biphenyl aldehyde was mixed with 0.3 ml of 2-hydroxyacetophenone in 30 ml of ethanol. In a separate flask, 2.0 gms of NaOH was dissolved in 10 ml of aq. ethyl alcohol (50%). An NaOH solution was slowly added to the aldehyde solution. The resulting solution slowly changed its color from green to yellow to dark red. The rest of the reaction was carried out according to the method described in Example 1(b) above, producing 4'styryl, 3-hydroxyflavone.

EXAMPLE 3

4'(4"vinyl)biphenylmethane, 3-hydroxyflavone a) 4-bromomethyl Benzaldehyde 4-bromomethyl benzaldehyde was synthesized in two steps.

(i) Synthesis of 1-(bromo) toluenitrile: 4-toluenitrile (0.1 mole) was added to a flask containing N-bromosuccinamide (0.11 mole) and 500 mg of dibenzoyl peroxide in 200 ml of carbon tetrachloride. The reaction mixture was refluxed under nitrogen overnight. The reaction mixture was filtered and the filtrate was concentrated under reduced pressure. Product was recovered by precipitation in 300 ml of hexane. The product was purified by recrystallization from chloroform. The yield of the product was 60%.

(ii) Synthesis of 4-bromomethyl benzaldehyde: A solution of 0.05 moles of diisobutyl aluminium hydride was dropwise added to a flask containing 0.05 moles of 1-(bromo) toluenitrile in 100 ml of benzene at 0° C. The reaction mixture was stirred overnight under nitrogen atmosphere. The reaction was terminated by pouring the entire reaction mixture into dil.HCl in an icebath. The product was isolated by solvent extraction with solvent ether. The ether layer was dried over anhyd. $MgSO_4$ and the ether layer was concentrated under reduced pressure. The product was recovered by precipitation in pentane. The product was purified by recrystallization from pentane. The yield of 4-bromomethyl benzaldehyde was 70%.

b) 4'vinyl, 4-aldehyde Diphenylmethane 4-trimethyltin styrene may be combined with 4-bromomethyl benzaldehyde following the procedure set forth in Example 2(b) above to produce 4'vinyl, 4-aldehyde diphenylmethane.

c) 4'(4"vinyl)biphenylmethane, 3-hydroxyflavone

4'vinyl, 4-aldehyde diphenylmethane may be combined with 2-hydroxyacetophenone according to the procedures set forth in Example 1(b) above to produce 4'(4"vinyl)biphenylmethane, 3-hydroxyflavone.

EXAMPLE 4

Poly(vinyl)-3-hydroxyflavone

Polymerization reactions of vinyl-3-hydroxyflavone were carried out in THF at 55° C. using azobisisobutyronitrile (AIBN) as a radical initiator. 500 mg of 4'vinyl-3-hydroxyflavone monomer was transferred to a polymerization tube containing 25 mg of AIBN. 5 ml of dry THF was then added. Monomer was partially soluble in THF at this stage. The polymerization tube was then sealed under high vacuum ($10^{-4}$ torr) after repeated freeze-thaw-pump cycles. Monomer was fully soluble in THF at 55° C. Polymerization was carried out for 72 hrs. The reaction was then stopped by breaking the seal and pouring the contents into ethyl alcohol. A yellow precipitate was obtained and was filtered and washed several times with hot ethyl alcohol. Polymer was purified by dissolving it in THF and precipitating it in ethyl alcohol twice. A 300 mg (approximately 60%) yield of poly(vinyl)-3-hydroxyflavone was obtained.

EXAMPLE 5

Poly(vinyl)-3-hydroxyflavone/polystyrene Copolymer

Copolymers containing different weight percentages of 4'vinyl-3-hydroxyflavone were synthesized using AIBN as a radical initiator. Copolymers were prepared having 0.1, 1.0 and 10% by weight infeed of 4'vinyl-3HF. In a typical procedure, 500 mg of 4'vinyl-3HF was mixed with 5 ml of styrene and 5 ml of THF containing 10 mg of AIBN in a polymerization tube. Monomer was partially soluble in THF at this stage. The polymerization tube was then sealed under high vacuum ($10^{-4}$ torr) after repeated freeze-thaw-pump cycles. The monomer was fully soluble in THF once it was warmed to a polymerization temperature of 60° C. When the desired conversion (less than 20%) was reached, the polymerization reaction was stopped by breaking the seal and pouring the contents into ethyl alcohol. A yellow precipitate (poly(vinyl)-3-hydroxy flavone/polystyrene copolymer) was obtained and was filtered and washed several times with hot ethyl alcohol. The copolymer was purified by dissolving it in THF and precipitating it in hot ethyl alcohol twice. Finally the copolymer was filtered and dried in vacuo for 24 hrs. Yield of the copolymer was approximately 1 gm (less than 20%).

EXAMPLE 6

The scintillating properties of poly(4-vinyl)-3HF were demonstrated by placing a film of the material in a 3 MeV electron beam. The film of poly(4-vinyl)-3HF was observed to scintillate brightly.

A determination of the absorption and emission behavior of vinyl 3HF monomer and polymer was made in comparison with 3HF using a spectrometer and a fluorimeter. The results of these tests are reported in Table 1.

TABLE 1

| | Absorption maximum, nm | Emission Maximum, nm |
|---|---|---|
| 3HF | 345 | 528 |
| 4-vinyl 3HF | 355 | 541 |
| poly(4-vinyl 3HF) | 350 | 536 |

The tests conducted on 3HF, vinyl 3HF and polyvinyl 3HF indicate that the absorption coefficient of vinyl 3HF and polyvinyl 3HF is about twice that of 3HF. The scintillating properties of these materials were demonstrated to be similar.

EXAMPLE 7

3-Hydroxy-2-thienylchromone

A solution of 3 g (22.2 mmol) of 2-hydroxyacetophenone, 2.5 g (22.2 mmol) of 2-thiophenecarboxaldehyde and 3 g NaOH (in 15 ml of water) in 50 ml of ethanol was stirred for 12 hours before the solution was poured into 300 ml of water. The resulting mixture was neutralized with dilute HCl to yield a chalcone. The yellow precipitate obtained was filtered and dried. The product was purified by recrystallized from methylene chloride. Further oxidation of above chalcone was carried out with excess of $H_2O_2$ (30%) in ethanol under basic conditions for 12 hours. The resulting solution was poured into 300 ml water and acidified with dilute HCl. Yellow precipitate obtained was filtered and dried. Product was recrystallized from THF/hexane mixture. Yield: 46%. Quantum Yield: (1.25 relative to 3HF in methyl cyclohexane), Extinction Coefficient: $\epsilon_{max}$ ($M^{-1}cm^{-1}$)=22000. $\lambda_{max}$ (abs)=355 nm and $\lambda_{max}$ (em)=545 nm. MP=202°–203° C.

EXAMPLE 8

3-Hydroxy-3-thienylchromone

A solution of 3 g (22.2 mmol) of 2-hydroxyacetophenone, 2.5 g (22.2 mmol) of thiophene 3-carboxaldehyde and 3 g NaOH (in 15 ml of water) in 50 ml of ethanol was stirred for 12 hours before the solution was poured into 300 ml of water. The resulting mixture was neutralized with dilute HCl to yield a chalcone. The yellow precipitate obtained was filtered and dried. The product was purified by recrystallized from methylene chloride. Further oxidation of above chalcone was carried out with excess of $H_2O_2$ (30%) in ethanol under basic conditions for 12 hours. The resulting solution was poured into 300 ml water and acidified with dilute HCl. Yellow precipitate obtained was filtered and dried. Product was recrystallized from THF/hexane mixture. Yield: 36%. Quantum Yield: (1.8 relative to 3HF in methyl cyclohexane), Extinction coefficient: $\epsilon_{max}$ ($M^{-1}cm^{-1}$)=2000. $\lambda_{max}$ (abs)=343 nm and $\lambda_{max}$ (em)=526 nm. MP=195°–196° C.

EXAMPLE 9

4'-(β-Methylethenyl)-3-hydroxyflavone

A solution of 4.92 g (36.1 mmol) of 2-hydroxyacetophenone, 3.30 g (34.2 mmol) of β-methyl styrene, 4-carboxaldehyde (mixture of cis and trans isomers) and 8.15 g NaOH (in 15 ml of water) in 125 ml of ethanol was stirred for 12 hours before the solution was poured into 600 ml of water. The resulting mixture was neutralized with dilute HCl. The yellow precipitate obtained was filtered and dried. The chalcone was purified by recrystallized from methylene chloride. Further oxidation of above chalcone was carried out with excess of $H_2O_2$ (30%) in ethanol under basic conditions for 12 hours. The resulting solution was poured into 300 ml water and acidified with dilute HCl. Yellow precipitate obtained was filtered and dried. 3-hydroxy-4'-(β-ethenyl) flavone was recrystallized from THF/hexane mixture. Yield: 35%. Quantum Yield: (1.75 relative to 3HF in methyl cyclohexane), Extinction coefficient: $\epsilon_{max}$ ($M^{-1}cm^{-1}$)=24000. $\lambda_{max}$ (abs)=355 nm and $\lambda_{max}$ (em)=551 nm.

α-β substituted ethenyl were also prepared by the treatment of corresponding α-β substituted ethenyl aldehydes with 2-hydroxyacetophenone.

EXAMPLE 10

3-Hydroxy-4'-(α-methyl), ethenylphenyl) Flavone

A solution of 4.92 g (36.1 mmol) of 2-hydroxyacetophenone, 3.30 g (34.2 mmol) of ,4'-(α-methyl)ethenyl, biphenyl 4-carboxaldehyde and 8.15 g NaOH (in 15 ml of water) in 100 ml of ethanol was stirred for 12 hours before the solution was poured into 400 ml of water. The resulting mixture was neutralized with dilute HCl to yield a chalcone. The yellow precipitate obtained was filtered and dried. The chalcone was purified by recrystallized from methylene chloride. Further oxidation of above chalcone was carried out with excess of $H_2O_2$ (30%) in ethanol under basic conditions for 12 hours. The resulting solution was poured into 500 ml water and acidified with dilute HCl. Yellow precipitate obtained was filtered and dried. Product was recrystallized form THF/hexane mixture. Yield: 33%. Quantum Yield: (1.8 relative to 3HF in methyl cyclohexane), Extinction coefficient: $\epsilon_{max}$ ($M^{-1}cm^{-1}$)=36000. $\lambda_{max}$ (abs)=355 nm and $\lambda_{max}$ (em )=550 nm.

3 -hydroxy-4'-(β-methyl) ethenylphenyl) flavone was also prepared in a similar way using, 4'(β-methyl)ethenyl, biphenyl 4-carboxaldehyde and 2-hydroxyacetophenone.

EXAMPLE 11

3-Hydroxy-2-naphthylchromone

A solution of 6 g (4.4 mmol) of 2-hydroxyacetophenone, 6.88 g (4.44 mmol) of 2-nephthelene carboxaldehyde and 6 g NaOH (in 15 ml of water) in 100 ml of ethanol was stirred for 12 hours before the solution was poured into 600 ml of water. The resulting mixture was neutralized with dilute HCl to yield a chalcone. The yellow precipitate obtained was filtered and dried. The chalcone was purified by recrystallized from methylene chloride. Further oxidation of above chalcone was carried out with excess of $H_2O_2$ (30%) in ethanol under basic conditions for 12 hours. The resulting solution was poured into 300 ml water and acidified with dilute HCl. Yellow precipitate obtained was filtered and dried. Product was recrystallized from THF/hexane mixture. Yield: 43%. $\lambda_{max}$ (abs)=353 nm and $\lambda_{max}$ (em)=542 nm. MP=202° C.

EXAMPLE 12

2-(2-Furanyl)-3-hydroxy-4H-1-benzopyran-4-one

A solution of 4.92 g (36.1 mmol) of 2'-hydroxyacetophenone, 3.30 g (34.3 mmol) of 2-furaldehyde, 8.15 g NaOH (in 13 mL of water) and 100 mL MeOH was stirred for 24 hours before the solution was poured into 600 mL water. The resulting mixture was neutralized with dilute HCl and the yellow precipitate was collected by filtration. Recrystallization from MeOH gave a pure intermediate chalcone product. Further oxidation of the above chalcone was carried out with excess $H_2O_2$ (30%) in basic (NaOH aq.) MeOH solution for 12 hours. This solution was poured into water, and neutralized with dilute HCl. The resulting light yellow precipitate was collected by filtration and the pure desired product was obtained by recrystallization from MeOH with 26% overall yield. MP: 173°–174° C. Quantum yield (relative to 3-hydroxyflavone in $CH_2Cl_2$) 0.6. Extinction coefficient $\epsilon_{max}$ ($M^{-1}cm^{-1}$) 21,000. $\lambda_{max}$ (abs)=352 nm and $\lambda_{max}$ (em)=535 nm.

EXAMPLE 13

2-(3-Furanyl)-3-hydroxy-4H-1-benzopyran-4-one

A solution of 2.84 g (20.9 mmol) of 2'-hydroxyacetophenone, 2.00 g (20.8 mmol) of 3-furaldehyde, 4.23 g NaOH (in 10 mL of water) and 100 mL MeOH was stirred for 24 hours before the solution was poured into 1000 mL water. The resulting mixture was neutralized with dilute HCl and the yellow precipitate was collected by filtration. Recrystallization from MeOH gave a pure intermediate chalcone product. Further oxidation of the above chalcone was carried out with excess $H_2O_2$ (30%) in basic (NaOH aq.) MeOH solution for 3.5 hours. This solution was poured into water, and neutralized with dilute HCl. The resulting light yellow precipitate was collected by filtration and the pure desired product was obtained by recrystallization from MeOH with 14% overall yield. MP: 165°–166° C. Quantum yield (relative to 3-hydroxyflavone in $CH_2Cl_2$) 1.1. Extinction coefficient $\epsilon_{max}$ ($M^{-1}cm^{-1}$) 14,000. $\lambda_{max}$ (abs)=340 nm and $\lambda_{max}$ (em)=517 nm.

EXAMPLE 14

3-Hydroxy-2-(2-pyrrolyl)-4H-1-benzopyran-4-one

A solution of 5.77 g (42.4 mmol) of 2'-hydroxyacetophenone, 3.98 g (41.9 mmol) of pyrrole-2-carboxaldehyde, 6.44 g NaOH (in 20 mL of water) and 150 mL MeOH was stirred for 73 hours before the solution was poured into 600 mL water. The resulting mixture was neutralized with dilute HCl and the yellow precipitate was collected by filtration. Recrystallization from MeOH gave a pure intermediate chalcone product. Further oxidation of the above chalcone was carried out with excess $H_2O_2$ (30%) in basic (NaOH aq.) MeOH solution for 25.5 hours. This solution was poured into water, and neutralized with dilute HCl. The resulting light green precipitate was collected by filtration and the pure desired product was obtained by recrystallization from MeOH with 2% overall yield. MP: 201°–203° C. Quantum yield (relative to 3-hydroxyflavone in $CH_2Cl_2$) 1.6. Extinction coefficient $\epsilon_{max}$ ($M^{-1}cm^{-1}$) 22,000. $\lambda_{max}$ (abs)=375 nm and $\lambda_{max}$ (em)=535 nm.

EXAMPLE 15

Trans-3-hydroxy-2-(β-phenylvinyl)-4H-1-benzopyran-4-one

A solution of 5.00 g (36.7 mmol) of 2'-hydroxyacetophenone, 4.85 g (36.7 mmol) of trans-cinnamaldehyde, 11.10 g NaOH (in 20 mL of water) and 250 mL MeOH was stirred for 23 hours before the solution was poured into 1000 mL water. The resulting mixture was neutralized with dilute HCl and the yellow precipitate was collected by filtration. Recrystallization from MeOH gave a pure intermediate chalcone product. Further oxidation of the above chalcone was carried out with excess $H_2O_2$ (30%) in basic (NaOH aq.) MeOH solution for 12 hours. This solution was poured into water, and neutralized with dilute HCl. The resulting light yellow precipitate was collected by filtration and the pure desired product was obtained by recrystallization from MeOH with 7% overall yield. MP: 189°–191° C. Quantum yield (relative to 3-hydroxyflavone in $CH_2Cl_2$) 0.04. Extinction coefficient $\epsilon_{max}$ ($M^{-1}cm^{-1}$) 26,000. $\lambda_{max}$ (abs)=374 nm and $\lambda_{max}$ (em)=600 nm.

EXAMPLE 16

3-Hydroxy-2-(β,β-diphenylvinyl)-4H-1-benzopyran-4-one

A solution of 1.81 g (13.3 mmol) of 2'-hydroxyacetophenone, 2.75 g (13.2 mmol) of β-phenylcinnamaldehyde, 2.64 g NaOH (in 10 mL of water) and 100 mL MeOH was stirred for 24 hours before the solution was poured into 1000 mL water. The resulting mixture was neutralized with dilute HCl and the yellow precipitate was collected by filtration. Recrystallization from MeOH gave a pure intermediate chalcone product. Further oxidation of the above chalcone was carried out with excess $H_2O_2$ (30%) in basic (NaOH aq.) MeOH solution for 18 hours. This solution was poured into water, and neutralized with dilute HCl. The resulting light yellow precipitate was collected by filtration and the pure desired product was obtained by recrystallization from MeOH with 28% overall yield. MP: 215°–216° C. Quantum yield (relative to 3-hydroxyflavone in $CH_2Cl_2$) 0.004. Extinction coefficient $\epsilon_{max}$ ($M^{-1}cm^{-1}$) 23,000. $\lambda_{max}$ (abs)= 378 nm and $\lambda_{max}$ (em)=470 nm.

EXAMPLE 17

3-Hydroxy-2-(β-phenylethynyl)-4H-1-benzopyran-4-one

A solution of 2.50 g (19.0 mmol) of 2'-hydroxyacetophenone, 2.42 g (18.6 mmol) of phenylpropargyladehyde, 3.44 g NaOH (in 9 mL of water) and 50 mL MeOH was stirred for 16 hours before the solution was poured into 500 mL water. The resulting mixture was neutralized with dilute HCl and extracted with $CH_2Cl_2$. The solvent was removed from the organic phase. Column separation with $CH_2Cl_2$-petroleum ether (1:1) gave a pure intermediate chalcone product. Further oxidation of the above chalcone was carried out with excess $H_2O_2$ (30%) in basic (NaOH aq.) MeOH solution for 18 hours. This solution was poured into water, and neutralized with dilute HCl. The resulting light yellow precipitate was collected by filtration and the pure desired product was obtained by recrystallization from MeOH with 2% overall yield. MP: 153°–154° C. Quantum yield (relative to 3-hydroxyflavone in $CH_2Cl_2$) 1.6. Extinction coefficient $\epsilon_{max}$ ($M^{-1}cm^{-1}$) 21,000. $\lambda_{max}$ (abs)=372 nm and $\lambda_{max}$ (em)=540 nm.

EXAMPLE 18

3-Hydroxy-2-(4'-(2-(3-hydroxychromonyl))) phenyl-4H-1-benzopyran-4-one

A solution of 1.02 g (7.49 mmol) of 2'-hydroxyacetophenone, 0.49 g (3.65 mmol) of 1,4-benzodicarboxaldehyde, 1.5 g NaOH (in 5 mL of water) and 30 mL MeOH was stirred for 21 hours before the solution was poured into 200 mL water. The resulting mixture was neutralized with dilute HCl and the yellow precipitate was collected by filtration. Recrystalization from MeOH gave a pure intermediate chalcone product. Further oxidation of the above chalcone was carried out with excess $H_2O_2$ (30%) in basic (NaOH aq.) MeOH solution for 20 hours. This solution was poured into water, and neutralized with dilute HCl. The resulting light yellow precipitate was collected by filtration and the pure desired product was obtained by recrystallization from MeOH with 22% overall yield. MP: 385°–387° C. Quantum yield (relative to 3-hydroxyflavone in $CH_2Cl_2$) 1.2. Extinction coefficient $\epsilon_{max}$ ($M^{-1}cm^{-1}$) 36,000. $\lambda_{max}$ (abs)=380 nm and $\lambda_{max}$ (em)=560 nm.

EXAMPLE 19

3-Hydroxy-2-(3'-(2-(3-hydroxychromonyl))) phenyl-4H-1-benzopyran-4-one

A solution of 4.02 g (29.5 mmol) of 2'-hydroxyacetophenone, 1.94 g (14.5 mmol) of 1,3-benzodicarboxaldehyde, 6.67 g NaOH (in 15 mL of water) and 100 mL MeOH was stirred for 21 hours before the solution was poured into 800 mL water. The resulting mixture was neutralized with dilute HCl and the yellow precipitate was collected by filtration. Recrystallization from MeOH gave a pure intermediate chalcone product. Further oxidation of the above chalcone was carried out with excess $H_2O_2$ (30%) in basic (NaOH aq.) MeOH solution for 20 hours. This solution was poured into water, and neutralized with dilute HCl. The resulting light yellow precipitate was collected by filtration and the pure desired product was obtained by recrystallization from MeOH with 17% overall yield. MP: 316°–318° C. Quantum yield (relative to 3-hydroxyflavone in $CH_2Cl_2$) 1.2. Extinction coefficient $\epsilon_{max}$ ($M^{-1}cm^{-1}$) 26,000. $\lambda_{max}$ (abs)=345 nm and $\lambda_{max}$ (em)=525 nm.

EXAMPLE 20

3-Hydroxy-2-(2',5'-didecyloxy-3'-(2-(3-hydroxychromonyl)))phenyl-4H-1-benzopyran-4-one A solution of 1.07 g (7.86 mmol) of 2'-hydroxyacetophenone, 1.00 g (2.24 mmol) of 2,5-didecyloxy-1,4-benzodicarboxaldehyde, 2.43 g NaOH (in 10 mL of water) and 100 mL mixture of THF and MeOH (1:1) was stirred for 20 hours before the solution was poured into 500 mL water. The resulting mixture was neutralized with dilute HCl and extracted with hexanes and $CH_2Cl_2$. The residue of the organic phase after removal of solvents was separated on column with $CH_2Cl_2$-petroleum ether (3:1) which yielded pure intermediate chalcone product. Further oxidation of the above chalcone was carried out with excess $H_2O_2$ (30%) in basic (NaOH aq.) MeOH-THF solution for 18 hours. This solution was poured into water, and neutralized with dilute HCl. The resulting light yellow precipitate was collected by filtration and the pure desired product was obtained by recrystallization from MeOH with 17% overall yield. MP: 205°–206° C. Quantum yield (relative to 3-hydroxyflavone in $CH_2Cl_2$) 0.5. Extinction coefficient $\epsilon_{max}$ ($M^{-1}cm^{-1}$) 21,000. $\lambda_{max}$ (abs)=350 nm and $\lambda_{max}$ (em)=560 nm.

EXAMPLE 21

3-Hydroxy-2-phenyl-4H-1-benzopyridin-4-one

To a solution of 0.23 g (0.96 mmol) 3-hydroxy-2-phenyl-2H, 3H, 4H-1-benzopyridin-4-one, 0.94 g NaOH (in 4 mL water) and 35 mL MeOH was added 15 mL of $H_2O_2$ over ice bath. The yellow solution was then stirred at room temperature for 4 hours before the mixture was poured into 300 mL of water. The resulting mixture was extracted with $CH_2Cl_2$ and the solvent was removed from the organic phase. The resulting residue was recrystallized form toluene which gave the desired product in 17% yield. MP: 260°–262° C. Quantum yield (relative to 3-hydroxyflavone in $CH_2Cl_2$) 1.4. Extinction coefficient $\epsilon_{max}$ ($M^{-1}cm^{-1}$) 10,000. $\lambda_{max}$ (abs)= 343 nm and $\lambda_{max}$ (em)=510 nm.

In view of the above, it will be seen that the several objects of the invention are achieved.

As various changes could be made in the above compositions and processes without departing from the scope of the invention, it is intended that all matter contained in the above description be interpreted as illustrative and not in a limiting sense.

What is claimed is:

1. A chromophore of the formula:

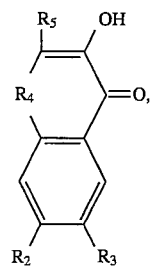

wherein $R_2$ and $R_3$ are independently hydrogen, alkyl, aryl, cyano, nitro, or, halo $R_4$ is O or N—H, and $R_5$ is thienyl, naphthyl, furanyl, pyrrolyl, diphenyl vinyl, phenyl ethynyl, hydroxy chromonyl phenyl, didecyloxy hydroxy chromonyl phenyl, phenyl or

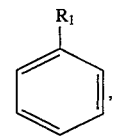

wherein $R_1$ is vinyl, vinyl phenyl, vinyl benzyl, alkyl ethenyl, or alkyl phenyl ethenyl, provided that when $R_5$ is phenyl and $R_2$ and $R_3$ are hydrogen, $R_4$ is N—H.

2. A chromophore as set forth in claim 1 wherein $R_4$ is O and $R_5$ is thienyl.

3. A chromophore as set forth in claim 2 wherein $R_5$ is 2-thienyl, and $R_2$ and $R_3$ are hydrogen.

4. A chromophore as set forth in claim 2 wherein $R_5$ is 3-thienyl, and $R_2$ and $R_3$ are hydrogen.

5. A chromophore as set forth in claim 1 wherein $R_4$ is O and $R_5$ is naphthyl.

6. A chromophore as set forth in claim 5 wherein $R_5$ is 1-naphthyl, and $R_2$ and $R_3$ are hydrogen.

7. A chromophore as set forth in claim 5 wherein $R_5$ is 2-naphthyl, and $R_2$ and $R_3$ are hydrogen.

8. A chromophore as set forth in claim 1 wherein $R_4$ is O and $R_5$ is furanyl.

9. A chromophore as set forth in claim 8 wherein $R_5$ is 2-furanyl, and $R_2$ and $R_3$ are hydrogen.

10. A chromophore as set forth in claim 8 wherein $R_5$ is 3-furanyl, and $R_2$ and $R_3$ are hydrogen.

11. A chromophore as set forth in claim 1 wherein $R_4$ is O and $R_5$ is pyrrolyl.

12. A chromophore as set forth in claim 11 wherein $R_5$ is 2-pyrrolyl and $R_2$ and $R_3$ are hydrogen.

13. A chromophore of the formula:

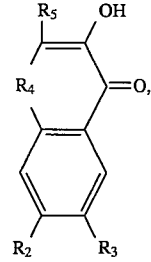

wherein $R_2$ and $R_3$ are independently hydrogen, alkyl, aryl, cyano, nitro, halo or an ether group, $R_4$ is N—H, and $R_5$ is phenyl vinyl.

14. A chromophore as set forth in claim 13 comprising trans-3-hydroxy-2-(β-phenyl vinyl)-4H-1-benzopyran-4-one.

15. A chromophore as set forth in claim 1 wherein $R_4$ is O and $R_5$ is diphenyl vinyl.

16. A chromophore as set forth in claim 15 comprising 3-hydroxy-2-(β,β-diphenylvinyl)-4H-1-benzopyran-4-one.

17. A chromophore as set forth in claim 1 wherein $R_4$ is O and $R_5$ is phenyl ethynyl.

18. A chromophore as set forth in claim 17 comprising 3-hydroxy-2-(β-phenylethynyl)-4H-1-benzopyran-4-one.

19. A chromophore as set forth in claim 1 wherein $R_4$ is O and $R_5$ is hydroxy chromonyl phenyl.

20. A chromophore as set forth in claim 19 comprising 3-hydroxy-2-(4'-(2-(3-hydroxychromonyl)))phenyl-4H-1-benzopyran-4-one or 3-hydroxy-2-(3'-(2-(3-hydroxychromonyl)))phenyl-4H-1-benzopyran-4-one.

21. A chromophore as set forth in claim 1 wherein $R_4$ is O and $R_5$ is didecyloxy hydroxy chromonyl phenyl.

22. A chromophore as set forth in claim 21 comprising 3-hydroxy-2-(2',5'-didecyloxy-3'-(2-3-hydroxychromonyl)))phenyl-4H-1 -benzopyran-4-one.

23. A chromophore as set forth in claim 1 wherein $R_4$ is N—H and $R_5$ is phenyl.

24. A chromophore as set forth in claim 23 comprising 3-hydroxy-2-phenyl-4H-1-benzopyridin-4-one.

25. A chromophore of the formula:

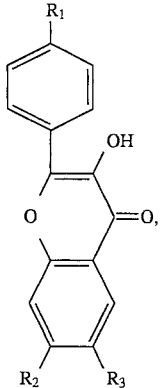

wherein $R_1$ is vinyl, vinyl phenyl, vinyl benzyl, alkyl ethenyl, or alkyl phenyl ethenyl, and $R_2$ and $R_3$ are independently hydrogen, alkyl, aryl, cyano, nitro, halo, or an ether group.

26. A chromophore as set forth in claim 25 wherein $R_1$ is alkyl ethenyl.

27. A chromophore as set forth in claim 26 comprising 4'-(β-methylethenyl)-3-hydroxyflavone.

28. A chromophore as set forth in claim 25 wherein $R_1$ is alkyl phenyl ethenyl.

29. A chromophore as set forth in claim 28 comprising 3-hydroxy-4'-(α-methyl), ethenylphenyl) flavone or 3-hydroxy-4'-(β-methyl), ethenylphenyl) flavone.

30. A chromophore as set forth in claim 25 wherein $R_1$ is vinyl, α-methyl vinyl, vinyl phenyl or vinyl benzyl.

31. A chromophore as set forth in claim 30 wherein $R_1$ is vinyl or α-methyl vinyl.

32. A chromophore as set forth in claim 31 wherein $R_2$ and $R_3$ are hydrogen.

33. A chromophore as set forth in claim 30 wherein $R_1$ is vinyl phenyl or vinyl benzyl.

34. A chromophore as set forth in claim 33 wherein $R_2$ and $R_3$ are hydrogen.

35. A chromophore of the formula:

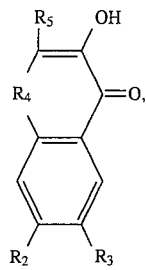

wherein $R_2$ is alkyl, aryl, cyano, nitro, halo or an ether group, $R_3$ is methyl, $R_4$ is O, and $R_5$ is phenyl vinyl.

36. A chromophore of the formula:

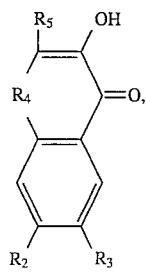

wherein $R_2$ is hydrogen, $R_3$ is hydrogen, alkyl other than methyl, aryl, cyano, nitro, halo or an ether group, $R_4$ is O, and $R_5$ is phenyl vinyl.

37. A chromophore of the formula:

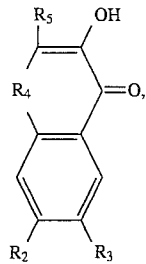

wherein $R_2$ and $R_3$ are both ether groups, $R_4$ is N—H, and $R_5$ is thienyl, naphthyl, furanyl, pyrrolyl, phenyl vinyl, diphenyl vinyl, phenyl ethynyl, hydroxy chromonyl phenyl, didecyloxy hydroxy chromonyl phenyl, phenyl or

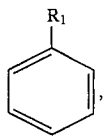

wherein $R_1$ is vinyl, vinyl phenyl, vinyl benzyl, alkyl ethenyl, or alkyl phenyl ethenyl.

* * * * *

UNITED STATES PATENT AND TRADEMARK OFFICE
CERTIFICATE OF CORRECTION

PATENT NO. : 5,552,551

DATED : September 3, 1996

INVENTOR(S) : Joseph B. Schlenoff, Kurtis F. Johnson, Jayesh Dharia and Feng Gao It is certified that error appears in the above-identified patent and that said Letters Patent is hereby corrected as shown below:

On the title page "[22] Filed: July 26, 1995" should read -- [22] Filed: July 26, 1993 --.

In column 25, Claim 22, line 18 "4H-1 -benzopyran" should read -- 4H-1-benzopyran --.

Signed and Sealed this

Second Day of September, 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,552,551
DATED : September 3, 1996
INVENTOR(S) : Joseph B. Schlenoff; Kurtis F. Johnson; Jayesh Dharia; Feng Gao It is certified that error appears in the above-identified patent and that said Letters Patent is hereby corrected as shown below:

Column 1, line 4, insert the following:

This invention was made with Government support under DOE Grant No. DE-FG05-87ER40319 awarded by the United States Department of Energy. The Government has certain rights in the invention.

Signed and Sealed this

Ninth Day of June, 1998

Attest:

BRUCE LEHMAN

Attesting Officer

Commissioner of Patents and Trademarks